(12) United States Patent
Stahmann et al.

(10) Patent No.: US 6,363,278 B1
(45) Date of Patent: Mar. 26, 2002

(54) CARDIAC RHYTHM MANAGEMENT SYSTEM WITH STAGGERED PULSES FOR COORDINATION THERAPY

(75) Inventors: Jeffrey E. Stahmann, Ramsey; Andrew P. Kramer, Stillwater; Julio C. Spinelli, Shoreview, all of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/549,862

(22) Filed: Apr. 14, 2000

(51) Int. Cl.[7] ............................................. A61N 1/368
(52) U.S. Cl. ................................................... 607/9
(58) Field of Search .......................... 607/9, 123, 27, 607/11–14; 600/509

(56) References Cited

U.S. PATENT DOCUMENTS

| | | | |
|---|---|---|---|
| 3,871,363 A | 3/1975 | Day ....................... 128/2.06 R |
| 4,147,990 A | 4/1979 | Dokus et al. ................. 330/11 |
| 4,319,197 A | 3/1982 | Trummer ..................... 330/11 |
| 4,856,524 A | 8/1989 | Baker, Jr. ............. 128/419 PG |
| 4,940,052 A | 7/1990 | Mann et al. .......... 128/419 PG |
| 5,033,473 A | 7/1991 | Wang et al. ................ 128/696 |
| 5,206,602 A | 4/1993 | Baumgartner et al. ......... 330/9 |
| 5,209,228 A | 5/1993 | Cano et al. ............ 128/419 PT |
| 5,293,169 A | 3/1994 | Baumgartner et al. ...... 341/172 |
| 5,329,281 A | 7/1994 | Baumgartner et al. ...... 341/139 |
| 5,337,230 A | 8/1994 | Baumgartner et al. ...... 364/138 |
| 5,382,956 A | 1/1995 | Baumgartner et al. ....... 341/155 |
| 5,391,192 A | 2/1995 | Lu et al. ........................ 607/28 |
| 5,431,696 A | 7/1995 | Atlee, III .................... 607/124 |
| 5,458,623 A | 10/1995 | Lu et al. ........................ 607/28 |
| 5,467,090 A | 11/1995 | Baumgartner et al. ....... 341/155 |
| 5,507,782 A | 4/1996 | Kieval et al. ................... 607/9 |
| 5,514,163 A | 5/1996 | Markowitz et al. ............ 607/9 |
| 5,527,347 A | 6/1996 | Shelton et al. ................. 607/9 |
| 5,534,016 A | 7/1996 | Boute ............................. 607/9 |
| 5,549,652 A | 8/1996 | McClure et al. .............. 607/28 |
| 5,578,064 A | 11/1996 | Prutchi ......................... 607/19 |
| 5,626,620 A | 5/1997 | Kieval et al. ................... 607/9 |
| 5,716,383 A | 2/1998 | Kieval et al. ................... 607/9 |
| 5,749,906 A | 5/1998 | Kieval et al. ................... 607/9 |
| 5,782,884 A | 7/1998 | Stotts et al. .................. 607/17 |
| 5,902,324 A | 5/1999 | Thompson et al. ............. 607/9 |
| 5,961,468 A | 10/1999 | Emmrich .................... 600/510 |

Primary Examiner—Scott M. Getzow
(74) Attorney, Agent, or Firm—Schwegman, Lundberg, Woessner & Kluth, P.A.

(57) ABSTRACT

A cardiac rhythm management system for coordination therapy includes a pulse generator to generate pacing and discharging of recharge pulses. A pulse delivery controller coupled to the pulse generator, times the delivery of the pacing and discharging of recharge pulses in a desired sequence. A therapy circuit coupled to the pulse delivery controller, receives the timed pulses from the pulse delivery controller and delivers the timed pulses to one or more electrodes disposed in or around a heart to communicate the timed pacing and discharging of recharge pulses to different sites of a heart, to avoid any interactions resulting from the electric fields surrounding the electrodes during a multiple site pacing required by the coordination therapy.

22 Claims, 15 Drawing Sheets

CARDIAC RHYTHM MANAGEMENT SYSTEM WITH STAGGERED PULSES FOR COORDINATION THERAPY

TECHNICAL FIELD OF THE INVENTION

This invention relates generally to cardiac rhythm management systems, and particularly, but not by way of limitation, to a cardiac rhythm management system, that provides staggered non-overlapping pulses for coordination therapy.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias uses drug therapy. Drugs are often effective at restoring normal heart rhythms. However, drug therapy is not always effective for treating arrhythmias of certain patients. For such patients, an alternative mode of treatment is needed. One such alternative mode of treatment includes the use of cardiac rhythm management system. Such a system may be implanted in a patient to deliver therapy to their heart.

Cardiac rhythm management systems include, among other things, pacemakers. Pacemakers deliver timed sequences of low energy electrical stimuli, called pace pulses, to the heart, such as via a transvenous lead wire or catheter (referred to as a "lead") having one or more electrodes disposed in or about the heart. Heart contractions are initiated in response to such pace pulses (this is referred to as "capturing" the pacing heart). By properly timing the delivery of pace pulses, the heart can be induced to contract in proper rhythm, greatly improving its efficiency as a pump. Pacemakers are often used to treat patient's hearts exhibiting bradyarrhythmias, that is, hearts that beat too slowly.

Cardiac rhythm management systems also include cardioverters or defibrillators that are capable of delivering higher energy electrical stimuli to the heart. Defibrillators may be used to treat patient's hearts exhibiting tachyarrhythmias, that is, hearts that beat too fast. Such too-fast heart rhythms also cause diminished blood circulation because the heart isn't allowed sufficient time to fill with blood before contracting to expel the blood, resulting in the heart pumping a reduced amount of blood. Such pumping by the heart is inefficient. A defibrillator is capable of delivering a high energy electrical stimulus. The high energy electrical stimulus interrupts the tachyarrhythmia, allowing the heart to reestablish a normal rhythm for the efficient pumping of blood. In addition to pacemakers, cardiac rhythm management systems also include, among other things, pacer/defibrillators that combine the functions of pacemakers and defibrillators, drug delivery devices, and any other systems or devices for diagnosing or treating cardiac arrhythmias.

Cardiac rhythm management systems are also used in the treatment of congestive heart failure. Congestive heart failure can occur when the left and right ventricles do not contract simultaneously, but rather, they contract one ventricle after the other ventricle. This reduces the pumping efficiency of the heart. Moreover, in the case of left bundle branch block, for example, different regions within the left ventricle may not contract together in a coordinated fashion. Generally congestive heart failure can be treated by biventricular coordination therapy that provides pacing pulses to both right and left ventricles. See. e.g., Mower, U.S. Pat. No. 4,928,688. Normally, intrinsic signals originate in the sinoatrial node in the upper right atrium, traveling through and depolarizing the atrial heart tissue such that resulting contractions of the right and left atria are triggered. The intrinsic atrial heart signals are received by the atrioventricular node which, in turn, triggers a subsequent ventricular intrinsic heart signal that travels through and depolarizes the ventricular heart tissue such that resulting contractions of the right and left ventricles are triggered substantially simultaneously.

One problem faced by cardiac rhythm management systems in treating congestive heart failure is that, coordination therapy may require issuing stimulation pace pulses simultaneously in more than one region of a heart to ensure these regions contract in a coordinated manner. For example, coordination therapy may require applying pacing stimulation to one or both ventricles or multiple sites within one or more ventricles in a pattern that coordinates the ventricular contraction sequence. Such therapy is believed to improve systolic function of patients with ventricular conduction disorders. During simultaneous pacing of multiple regions of the heart, the resulting electric fields generated between the pacing sites may interact. This may result in unwanted and unexpected currents between the pacing electrodes at different sites such as different chambers of the heart and can affect the ability of the pacing pulses to capture the heart at the simultaneous pacing sites. Such interactions can become greater when the coordination pacing pulses have different voltage amplitudes due to the resulting electric fields between the pacing sites. Another problem with issuing biventricular coordination pace pulses simultaneously in more than one chamber is that these interactions can result in very inefficient pacing methods, one example being that it may transform cathodal pacing pulse into anodal pacing pulse.

These interactions can increase when a bipolar right ventricular electrode configuration is used with a single left ventricular electrode. In this configuration, one of the right ventricular electrodes provides a common return path, for the right and left ventricular stimulations. During such interactions, the simultaneous biventricular capture cannot be assured if left ventricular and right ventricular capture is tested separately.

When the pace pulses are delivered to a heart, leftover charge (recharge pulses) from pacing regions is discharged from the heart. These recharge pulses may also interact with pace pulses or other recharge pulses at different heart locations. This too may result in unwanted interactions between different sites.

Generally simultaneous pacing of multiple regions of a heart can be advantageous in the treatment of congestive heart failure, however; such simultaneous pacing at different pacing sites may result in unwanted interactions between different pacing sites. These interactions may result in undesirable results, such as loss of capture at the pacing sites. Thus, there is a need to eliminate unwanted interactions between electrodes at different pacing sites of a heart.

SUMMARY

The above mentioned shortcomings, disadvantages and problems are addressed by the present subject matter, which will be understood by reading and studying the following specification. The present subject matter provides, among other things, a cardiac rhythm management system that eliminates interactions between electrodes at multiple pacing sites of a heart. This is accomplished by providing an offset between adjacent pacing and/or recharge pulses to electrodes in various regions of a heart to eliminate the interactions at different pacing sites. This improves the treatment for congestive heart failure by providing the required/programmed level of energy to the pacing sites. The present system provides an offset between pulses to eliminate the interactions during unichamber, bichamber, or multisite pacing with or without intersite stimulation delays to restore proper coordination between different chambers and between different intra chamber regions of the heart.

According to one aspect of the present subject matter, a pulse delivery controller receives pulses from a pulse generator and then delivers the pulses to multiple electrodes located at different pacing sites in a desired sequence to avoid any interactions between electric fields surrounding the electrodes during pulsing at different pacing sites. After delivering the pacing pulses, discharging of the recharge pulses begins from the respective pacing sites. During discharging, the pulse delivery controller further offsets recharge pulses to eliminate interactions between recharge and pacing pulses. Similar pulse sequencing takes place every subsequent cardiac cycle interval.

In one embodiment of providing coordination therapy, the system issues a time delay between the left and right ventricular pacing and recharge pulses to avoid any interactions between the leads. In another embodiment, the system issues a time delay between pulses (pace and/or recharge) associated with the right atrial, and right ventricular leads, and a time delay between pulses associated with right and left ventricular pulses to avoid any interactions between these leads. In another embodiment the system issues a time delay between pulses associated with left cardiac chamber electrode and the right cardiac chamber electrode to avoid any interactions between these leads. In another embodiment the system issues a time delay between pulses associated with right cardiac chamber electrode and the left cardiac chamber electrode to avoid any interactions between these leads.

Other aspects of the present subject matter will be apparent on reading the following detailed description of the invention and viewing the drawings that form a part thereof.

DETAILED DESCRIPTION

Figure 1:
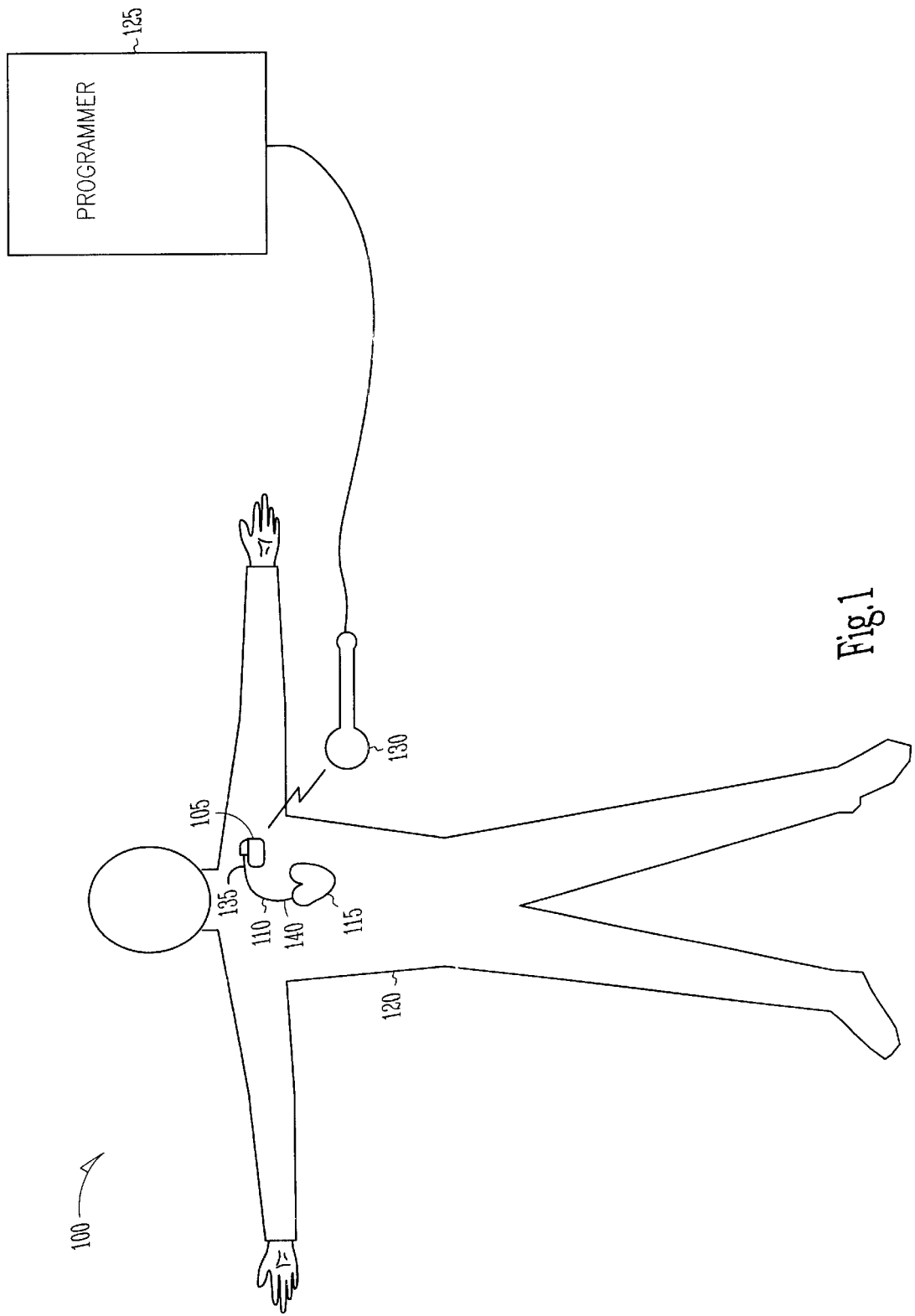
FIG. 1 is a schematic drawing illustrating generally one embodiment of portions of a cardiac rhythm management system and an environment in which it is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents. In the accompanying drawings, like numerals describe substantially similar components throughout the several views. Like numerals having different suffixes represent different instances of substantially similar components.

In this document, the term "offset" means, first and second pulses delivered to electrodes in various regions of a heart are timed such that there is a fractional time delay between an end of the delivery of the first pulse and a beginning of delivery of the second pulse such that the pulses are substantially simultaneous yet non-overlapping, to avoid any interactions between electric fields at various pacing sites, and to provide the required/programmed coordinated therapy.

In this document, the term "pulse delivery controller" is understood as the controller delivering the offset pulses to the electrodes in a desired sequence to avoid any interactions between electric fields during pulsing at various pacing sites. The term "timer" is also understood as the timer providing the offset pulses to the electrodes in the desired sequence to avoid interactions between electric fields during pulsing at various pacing sites.

Also in this document, the term "discharging of recharge pulse" is understood as, removal of an accumulated charge within the system or cardiac tissue, by generally reversing the current through the pacing circuit via a low amplitude, low duration recharge pulse.

The present methods and apparatus will be described in applications involving implantable medical devices including, but not limited to, implantable cardiac rhythm management systems such as pacemakers, cardioverter/defibrillators, pacer/defibrillators, and biventricular or other multi-site coordination devices. However, it is understood that the present methods and apparatus may be employed in unimplanted devices, including, but not limited to, external pacemakers, cardioverter/defibrillators, biventricular or other multi-site coordination devices, monitors, programmers and recorders.

This document describes, among other things, a cardiac rhythm management system providing a method and apparatus for offsetting but non-overlapping the pacing and recharge pulses to eliminate unwanted interactions between electrodes at various pacing sites.

One problem faced by cardiac rhythm management systems is that the coordination therapy may require issuing stimulation pace pulses simultaneously in more than one region of a heart to ensure these regions contract in a coordinated manner. For example, coordination therapy may require applying pacing stimulation to one or both ventricles or multiple sites within one or more ventricles in a pattern that coordinates the ventricular contraction sequence. Such therapy is believed to improve systolic function of patients with ventricular conduction disorders. During simultaneous pacing of multiple regions of the heart, the resulting electric fields generated between the pacing sites may interact. This may result in unwanted and unexpected currents between the pacing electrodes at different sites such as different chambers of the heart. Such interactions can have great implications when the coordination pacing pulses have different voltage amplitudes due to the resulting electric fields between the pacing sites. One such implication with issuing biventricular coordination pace pulses simultaneously in more than one chamber is that these interactions may transform cathodal pacing pulse into anodal pacing pulse.

The problem of interactions between pacing electrodes can become even greater when a bipolar right ventricular electrode configuration is used with a single left ventricular electrode. In such configuration, one of the right ventricular electrodes provides a common return path, for the right and left ventricular stimulations. Also due to these interactions, the simultaneous biventricular capture cannot be assured if left ventricular and right ventricular capture is tested separately.

Therefore, the present system advantageously delivers offset pacing pulses that are as close in time as feasible and yet non-overlapping to provide the required coordination therapy. Also the system advantageously offsets the discharging of the recharge pulses associated with the pacing pulses to eliminate any interactions between electric fields associated with pacing and recharge pulses. In one embodiment, the offset between pacing pulses is so small and physiologically insignificant that the propagation of resulting depolarization at different heart chambers are still acceptable to generate coordinated contraction of cardiac chambers. In one example, a three millisecond non-overlapping offset between the end of delivery of right cardiac chamber pacing pulse and the beginning of delivery of left cardiac chamber pacing pulse is sufficient to generate simultaneous contraction of the two cardiac chambers, and also this offset is sufficient to avoid any unwanted interactions between electrodes during pacing.

FIG. 1 is a schematic drawing illustrating generally, by way of example, but not by way of limitation, one embodiment in which the cardiac rhythm management system is used. In FIG. 1, system 100 includes an implantable cardiac rhythm management device 105, also referred to as an electronics unit, which is coupled by an intravascular endocardial lead 110, or other lead, to a heart 115 of patient 120. System 100 also includes an external programmer 125 providing wireless communication with device 105 using a telemetry device 130. Catheter lead 110 includes a proximal end 135, which is coupled to device 105, and a distal end 140, which is coupled to one or more portions of heart 115.

Figure 2:
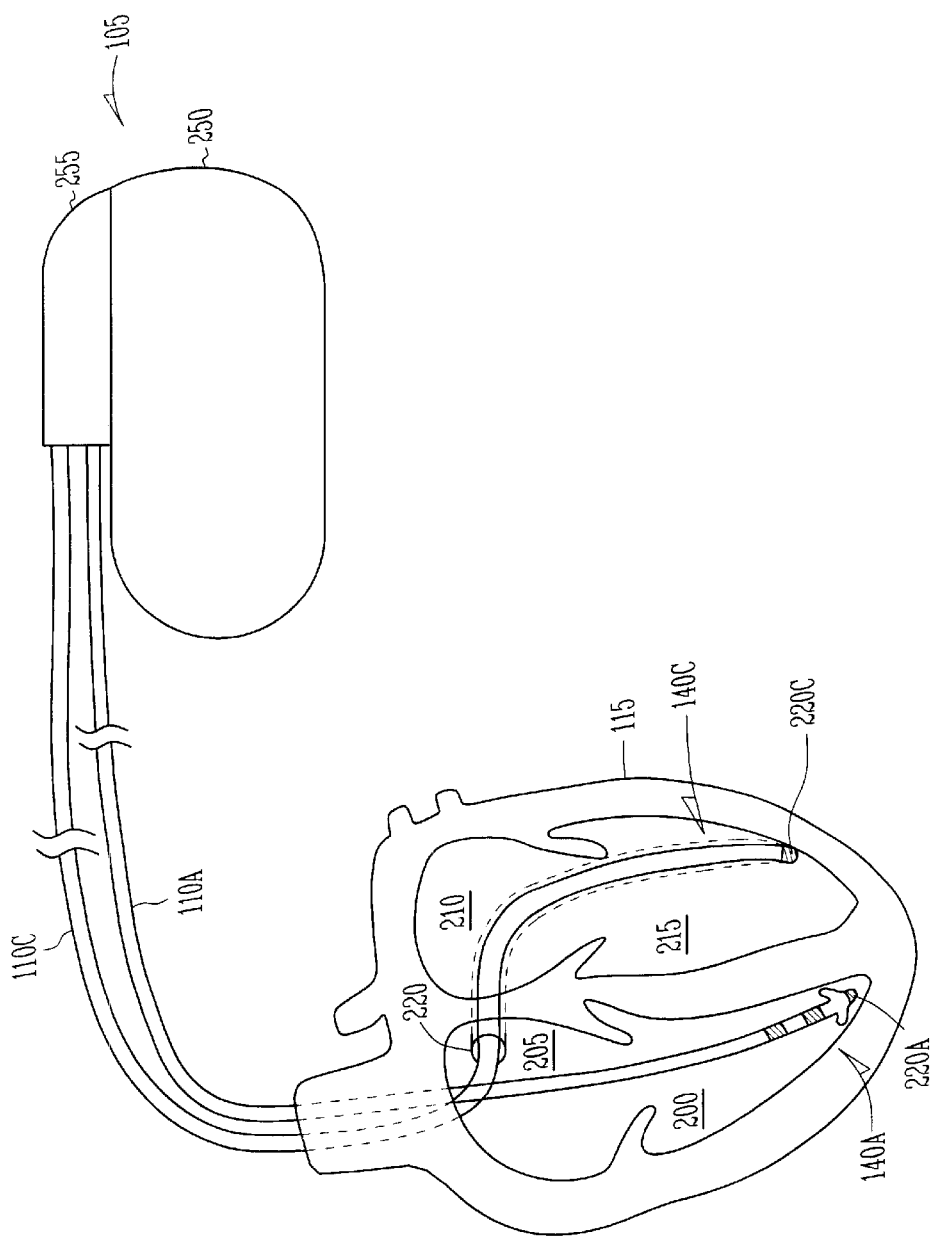
FIG. 2 is a schematic drawing illustrating generally one embodiment of portions of a cardiac rhythm management system coupled to a heart by left and right ventricular electrodes.

FIG. 2 is a schematic drawing illustrating generally, by way of example, but not by way of limitation, one embodiment of device 105 coupled by leads 110A and 110C to a heart 115, which includes a right atrium 205, a left atrium 210, a right ventricle 200 and a left ventricle 215. Device 105 includes components that are enclosed in a hermetically sealed enclosure, such as can 250. Additional electrodes may be located on the can 250, or on an insulating header 255, or on portions of device 105, for providing pacing and/or defibrillation energy in conjunction with the electrodes disposed in or around heart 115. In this embodiment, right ventricular lead 110A includes electrodes (electrical contacts) disposed in, around, or near right ventricle 200 of heart 115, such as ring electrode 140A or tip electrode 220A for delivering pacing therapy to the ventricle 200. Also in this embodiment is shown, left ventricular lead 110C disposed in, around, or near left ventricle 215 of the heart 115, such as tip electrode 220C or ring electrode 140C for delivering pacing therapy to the heart 115. The present method and apparatus will work in a variety of configurations and with a variety of electrical contacts or "electrodes."

Figure 3:
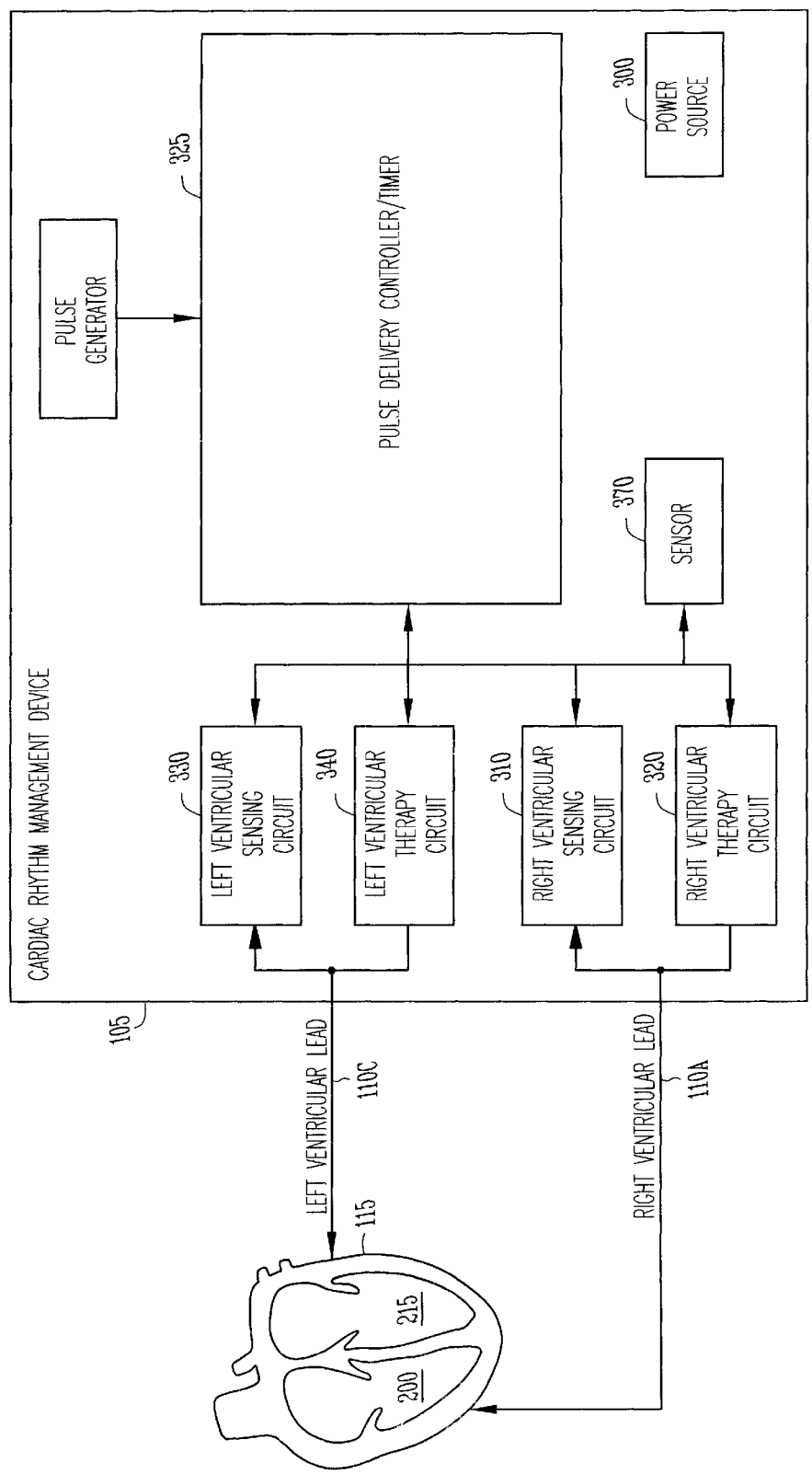
FIG. 3 is a schematic/block diagram illustrating generally one embodiment of portions of a cardiac rhythm management system showing interconnections between major functional components of the cardiac rhythm management device when using right and left ventricular electrodes coupled to a heart.

FIG. 3 is a schematic/block diagram illustrating generally, by way of example, but not by way of limitation, one embodiment of portions of device 105, coupled to a heart 115. In this embodiment, device 105 includes power source 300, left and right ventricular sensing circuits 330 and 310, a left ventricular a ventricular therapy circuits 340 and 320 providing coordination therapy to the heart, as appropriate, through the electrodes located at or near the ventricles 200 and 215, from a pulse delivery controller 325.

Right and left ventricular sensing circuits 310 and 330 are coupled by right and left ventricular leads 110A and 110C to the heart 115 for receiving, sensing, and/or detecting ventricular activations (also referred to as ventricular depolarizatons or R-waves), which correspond to ventricular contractions. Such ventricular heart signals include normal ventricular rhythms, and abnormal fibrillation, and other ventricular activity, such as irregular ventricular contractions resulting from conducted signals from atrial fibrillation. Ventricular sensing circuits provide one or more signals to pulse delivery controller 325 indicating, among other things, the presence of ventricular depolarizations, whether regular or irregular in rhythm.

Ventricular therapy circuits 320 and 340 provide ventricular pacing therapy, as appropriate, to electrodes located at or near the ventricles 200 and 215 of the heart 115 for obtaining resulting evoked ventricular depolarizations.

The pulse delivery controller 325, controls the delivery of coordination therapy, and provides the offset and non overlapping pacing pulses to the left and right ventricular electrodes, based on heart signals received from left and right ventricular sensing circuits 330 and 310. Pulse delivery controller 325 includes various modules, which are implemented either in hardware or as one or more sequences of steps carried out on a microprocessor or other microcontroller. It is understood that the various modules of pulse delivery controller 325 need not be separately embodied, but may be combined or otherwise implemented differently, such as in software/firmware.

In general terms, sensing circuits 310 and 330 sense electrical signals from heart tissue in contact with the catheter leads 110A and 110C to which these sensing circuits 310 and 330 are coupled. Sensing circuits 310 and 330 and/or pulse delivery controller 325 process these signals. Based on these sensed signals, pulse delivery controller 325 issues control signals to therapy circuits, such as ventricular coordination therapy circuits 320 and 340, if necessary, for the delivery of electrical energy (e.g., pacing and/or defibrillation pulses) to the appropriate electrodes of leads 110A and 110C. Pulse delivery controller 325 may include a microprocessor or other form of controller for execution of software and/or firmware instructions. The software of the pulse delivery controller 325 may be modified (e.g., by remote external programmer 125) to provide different parameters, modes, and/or functions for the implantable device 105 or to adapt or improve performance of device 105.

In one further embodiment, one or more sensors, such as sensor 370, may serve as inputs to pulse delivery controller 325 for adjusting the rate at which pacing or other therapy is delivered to heart 115. One such sensor 370 includes an accelerometer that provides an input to pulse delivery controller 325 indicating increases and decreases in physical activity, for which pulse delivery controller 325 increases and decreases pacing rate, respectively. Another such sensor includes an impedance measurement, obtained from body electrodes, which provides an indication of increases and decreases in the patient's respiration, for example, for which pulse delivery controller 325 increases and decreases pacing rate, respectively. Any other sensor 370 providing an indicated pacing rate can be used.

Figure 4:
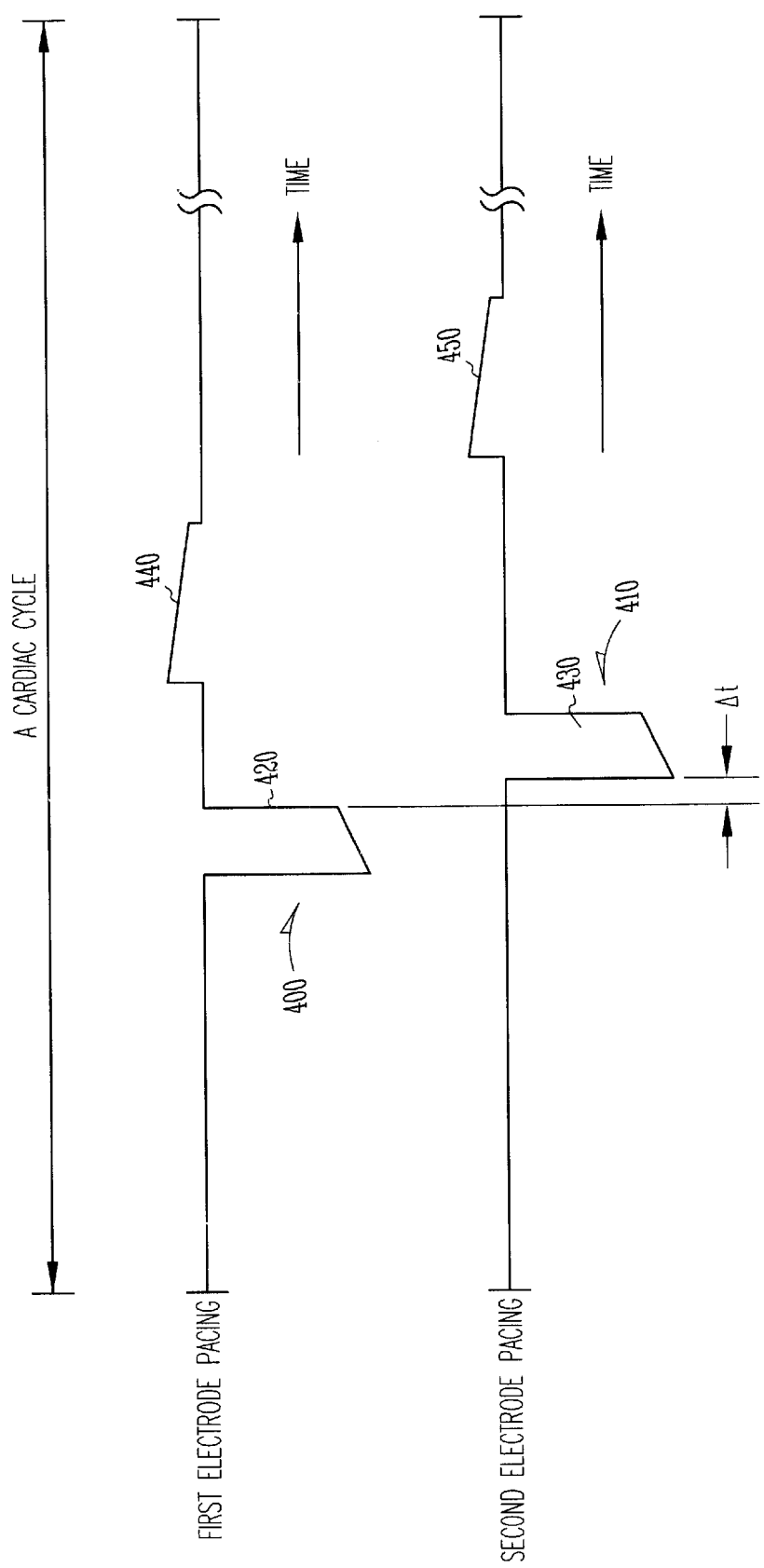
FIG. 4 is a schematic illustrating generally, by way of example, one embodiment of an offset issued by a pulse delivery controller between the pacing pulses associated with first and second electrodes.

FIG. 4 is a schematic illustrating generally, by way of example, but not by way of limitation, one embodiment of issuing an offset 'Δt' by the pulse delivery controller 325 between the end 420 of delivery of first pacing pulse 400 and beginning 430 of delivery of a second pacing pulse 410 to avoid any interactions between the first and second pacing pulses during a coordination therapy. This offset 'Δt' is generally a very small fractional time of a single cardiac cycle interval, and physiologically insignificant (offset 'Δt' is about 2 to 10 milliseconds in a cardiac cycle interval ranging between 324 to 2000 milliseconds), such that the propagation of resulting depolarizations at different heart chambers are still acceptable to generate coordinated contraction of heart chambers. Also shown is an offset between discharging of recharge pulses 440 and 450 associated with the first and second pacing pulses introduced by the pulse delivery controller 325 to avoid any interactions during the discharging of the recharge pulses 440 and 450. In one embodiment, the discharging of the recharge pulses takes place between pacing pulses as time allows and completing any unfinished portion after the pacing pulse with appropriate offsets in between the pacing and recharge pulses to avoid any interactions.

Figure 5:
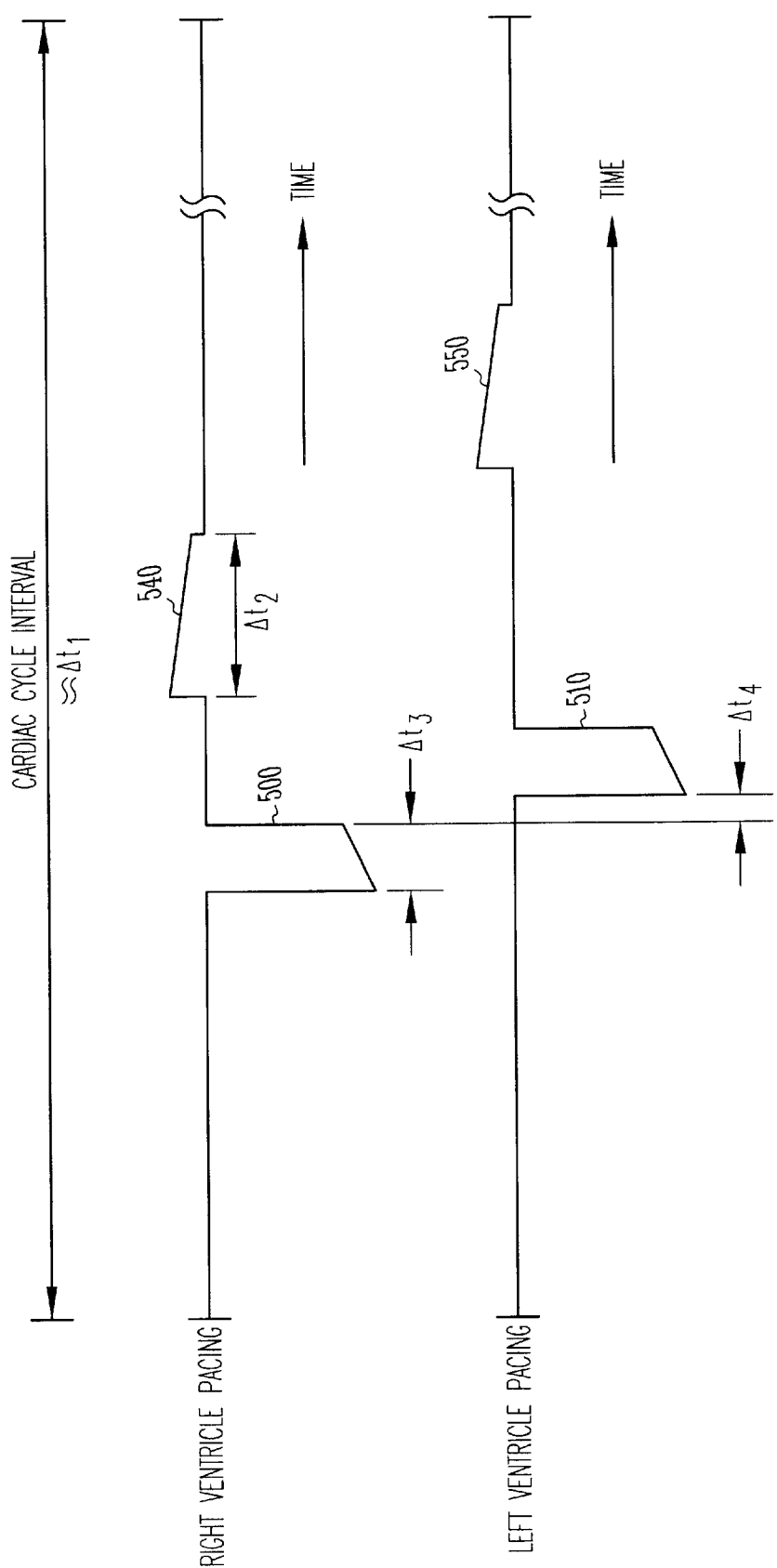
FIG. 5 is a schematic illustrating generally, by way of example, one embodiment of ranges of time delays and pulse duration issued during left and right ventricular pacing and discharging of recharge pulses.

FIG. 5 is a schematic illustrating generally, by way of example, but not by way of limitation, one embodiment of offset $\Delta_{t4}$ introduced between the left and right ventricular pacing pulses 500 and 510 of about 2 to 10 milliseconds to avoid any interactions between electric fields surrounding the electrodes. Also shown in this embodiment, by way of example, are the pacing pulse duration $\Delta_{t3}$ ranging between 0.05 to 2 milliseconds, the recharge pulse 540 duration $\Delta_{t2}$ ranging between 5 to 50 milliseconds, and the cardiac cycle interval $\Delta_{t1}$ ranging between 324 to 2000 milliseconds to avoid interactions between electric fields surrounding the electrodes during pacing 500 and 510 and discharging of recharge pulses 540 and 550 at various pacing sites of a heart.

Figure 6:
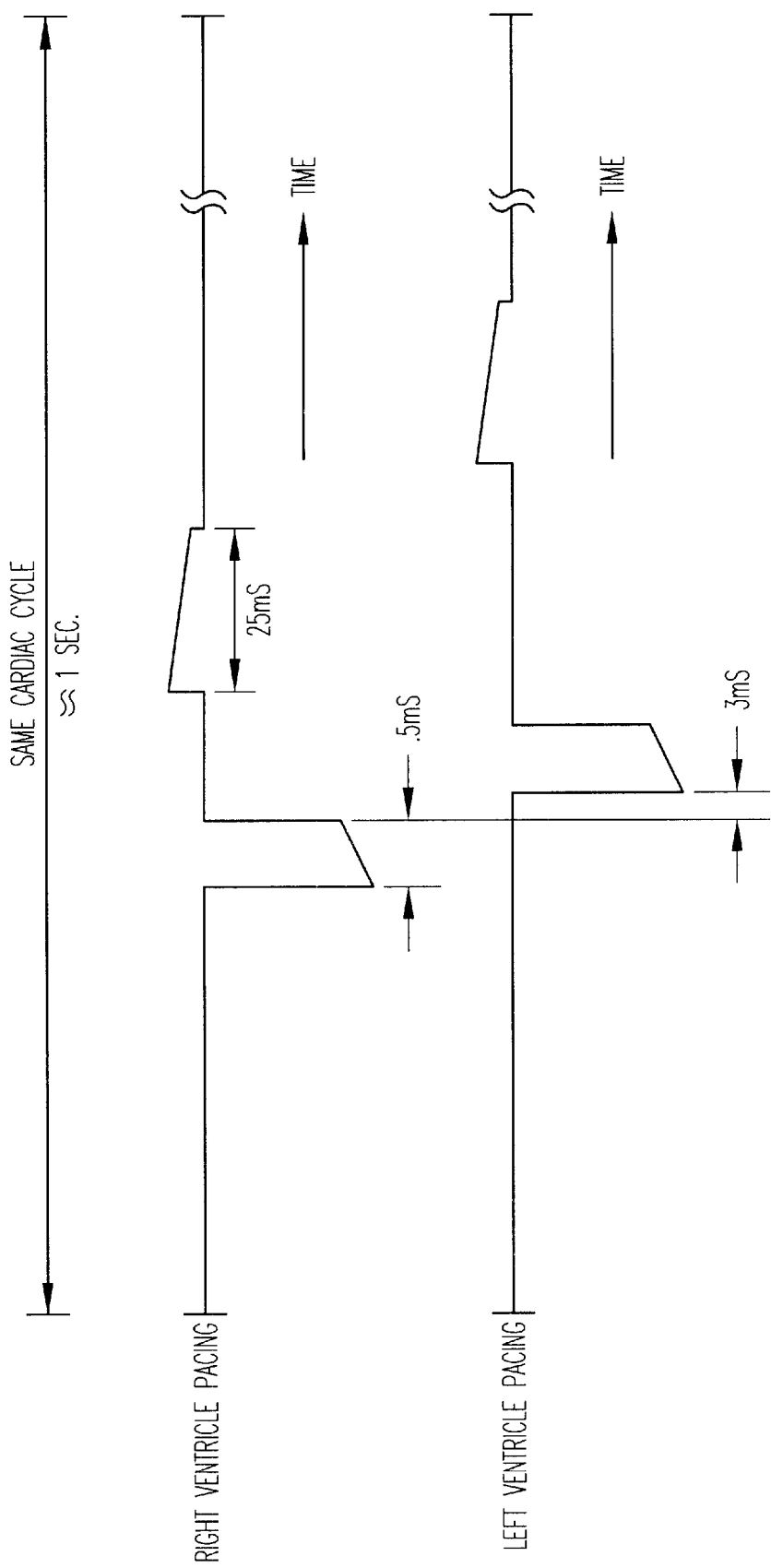
FIG. 6 is a schematic drawing illustrating generally, by way of example, one embodiment of time offsets used in a cardiac rhythm management system.

FIG. 6 is a schematic illustrating generally, by way of example, but not by way of limitation, one embodiment of a three millisecond offset issued between the right and left ventricular pacing pulses to generate the simultaneous contraction of the two heart chambers, and to avoid any unwanted interactions between electrodes during a coordination therapy.

Figure 7:
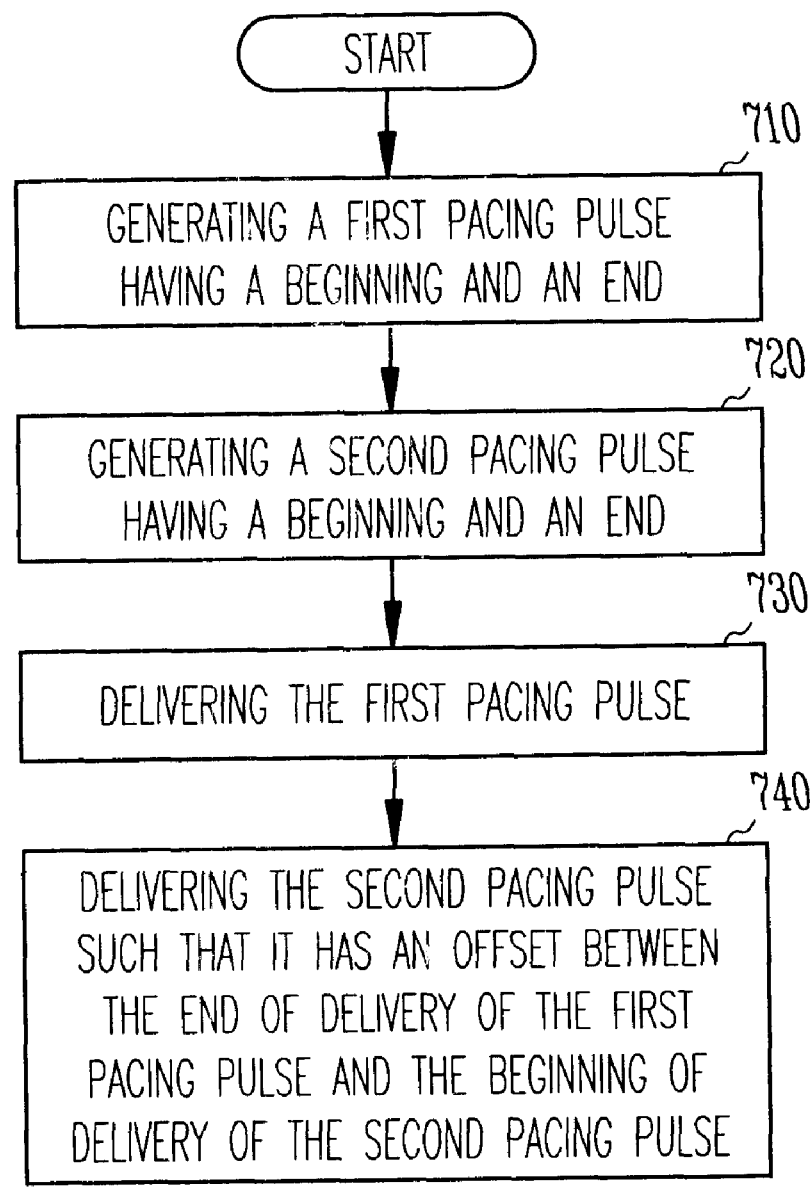
FIG. 7 is a flow chart illustrating generally, by way of example, an embodiment of the steps of providing a coordinated therapy.

FIG. 7 is a flow chart, illustrating generally, by way of example, but not by way of limitation, one embodiment 700 of the various steps included in providing a coordinated therapy to a heart. Upon generating first and second pacing pulses 710 and 720, a pulse delivery controller delivers the first pacing pulse 730, and then deliver the second pacing pulse having an offset between the end of delivery of the first pacing pulse and the beginning of delivery of the second pacing pulse to provide a coordinated therapy 740.

Figure 7A:
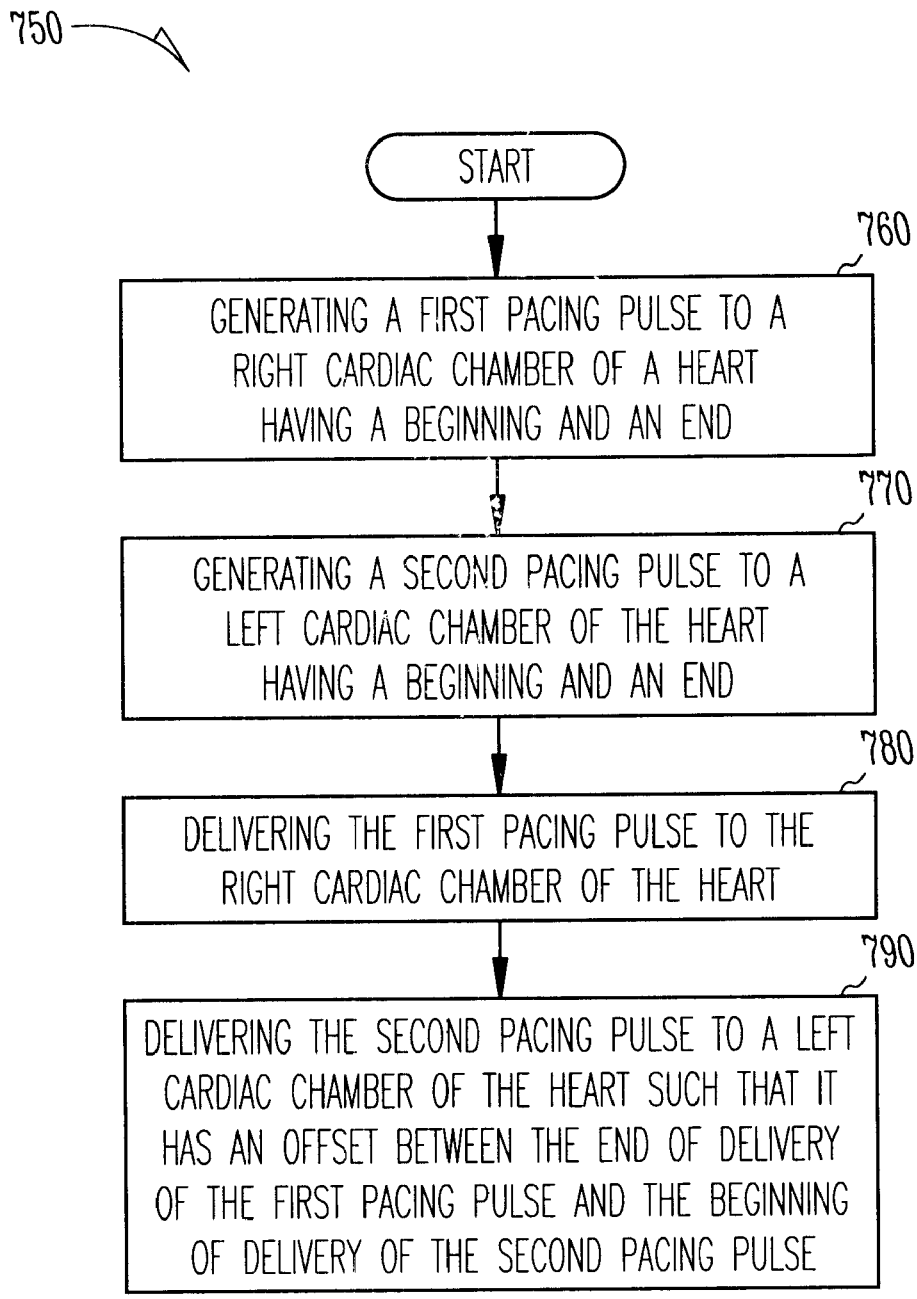
FIG. 7A is a flow chart illustrating generally, by way of example, another embodiment of the steps of providing a coordinated therapy.

FIG. 7A is a flow chart, illustrating generally, by way of example, but not by way of limitation, one embodiment of the various steps included in providing a coordinated therapy to a heart 750. Upon generating right and left cardiac chamber pacing pulses 760 and 770, a pulse delivery controller delivers the right cardiac chamber pacing pulse 780, and then delivers the left cardiac chamber pacing pulse at least 2 to 10 milliseconds after completing the delivery of the right cardiac chamber pacing pulse to a heart to avoid any interactions between the electric fields surrounding the electrodes during the right and left cardiac chamber pacing 790. In one embodiment, after completing the delivery of the left ventricular pacing pulse, the pulse deliver controller, discharges right and left cardiac chamber recharge pulses such that the discharge of the recharge pulse are non-overlapping with the right and left cardiac chamber pacing pulses. In one embodiment the discharging of the recharge pulses takes place between pacing pulses as time allows and completing any unfinished portion after the pacing pulse.

Figure 8:
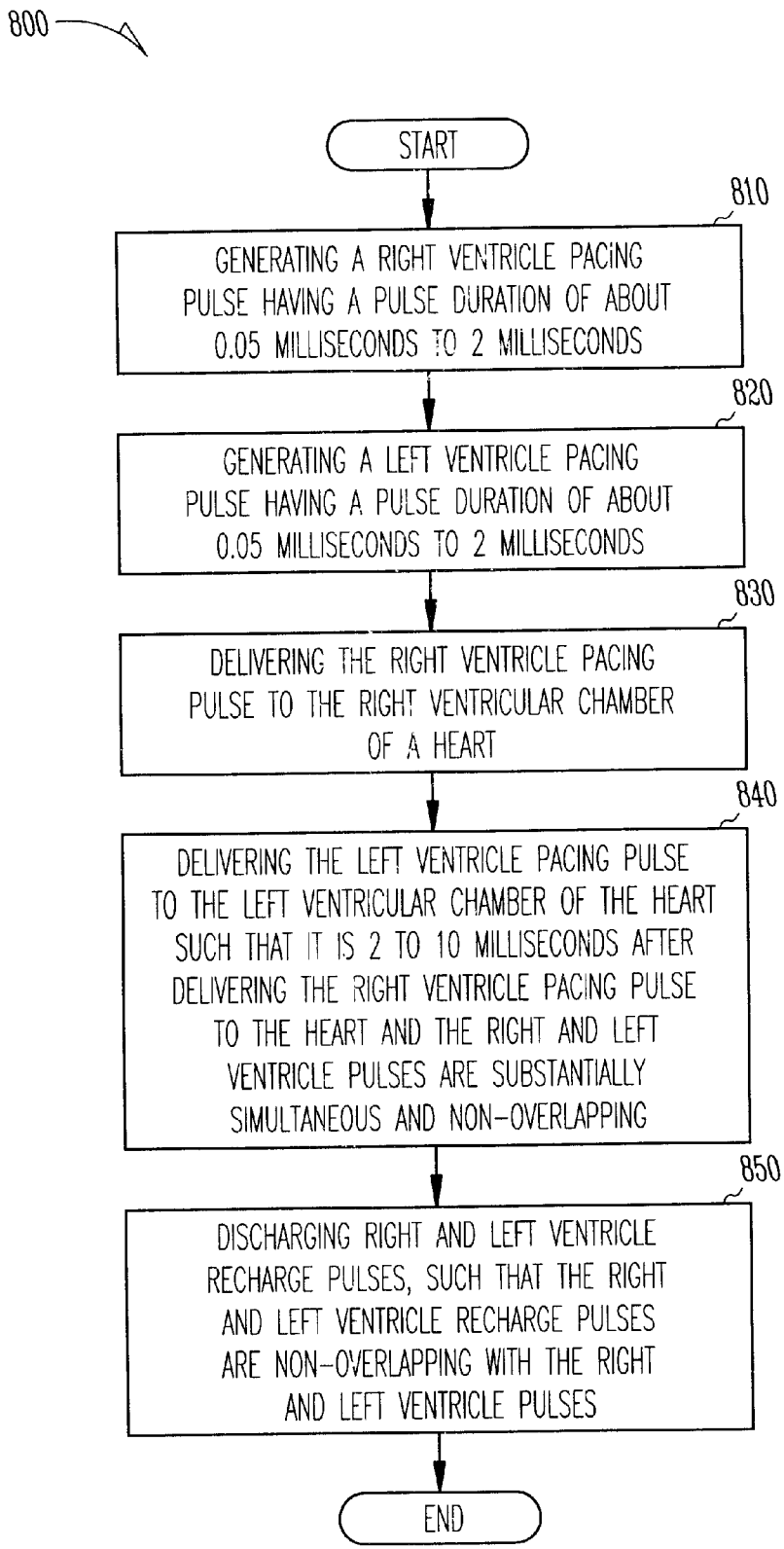
FIG. 8 is a flow chart illustrating generally, by way of example, another embodiment of the steps of providing a coordinated therapy.

FIG. 8 is a flow chart, illustrating generally, by way of example, but not by way of limitation, another embodiment 800 of the various steps included in providing a coordinated therapy to a heart. The first step in the process of providing the coordinated therapy to the heart includes generating a right ventricle pacing pulse having a pulse duration of about 0.05 to 2 milliseconds 810. Then generating a left ventricle pacing pulse having a pulse duration of about 0.05 to 2 milliseconds 820. After generating the right and left ventricle pacing pulses, a pulse delivery controller delivers the right ventricle pacing pulse to a right ventricular chamber of a heart at 830. The pulse delivery controller then delivers the left ventricle pacing pulse to a left ventricular chamber of the heart such that it is 2 to 10 milliseconds after delivering the right ventricle pacing pulse to the heart, and further the right and left ventricle pacing pulses are substantially simultaneous and non-overlapping to avoid any interactions between electric fields surrounding the electrodes during pacing 840. Then the pulse delivery controller discharges right and left ventricle recharge pulses, such that the right and left ventricle recharge pulses are non-overlapping with the right and left ventricle pacing to avoid any interactions between surrounding electrodes during discharging 850.

Figure 9:
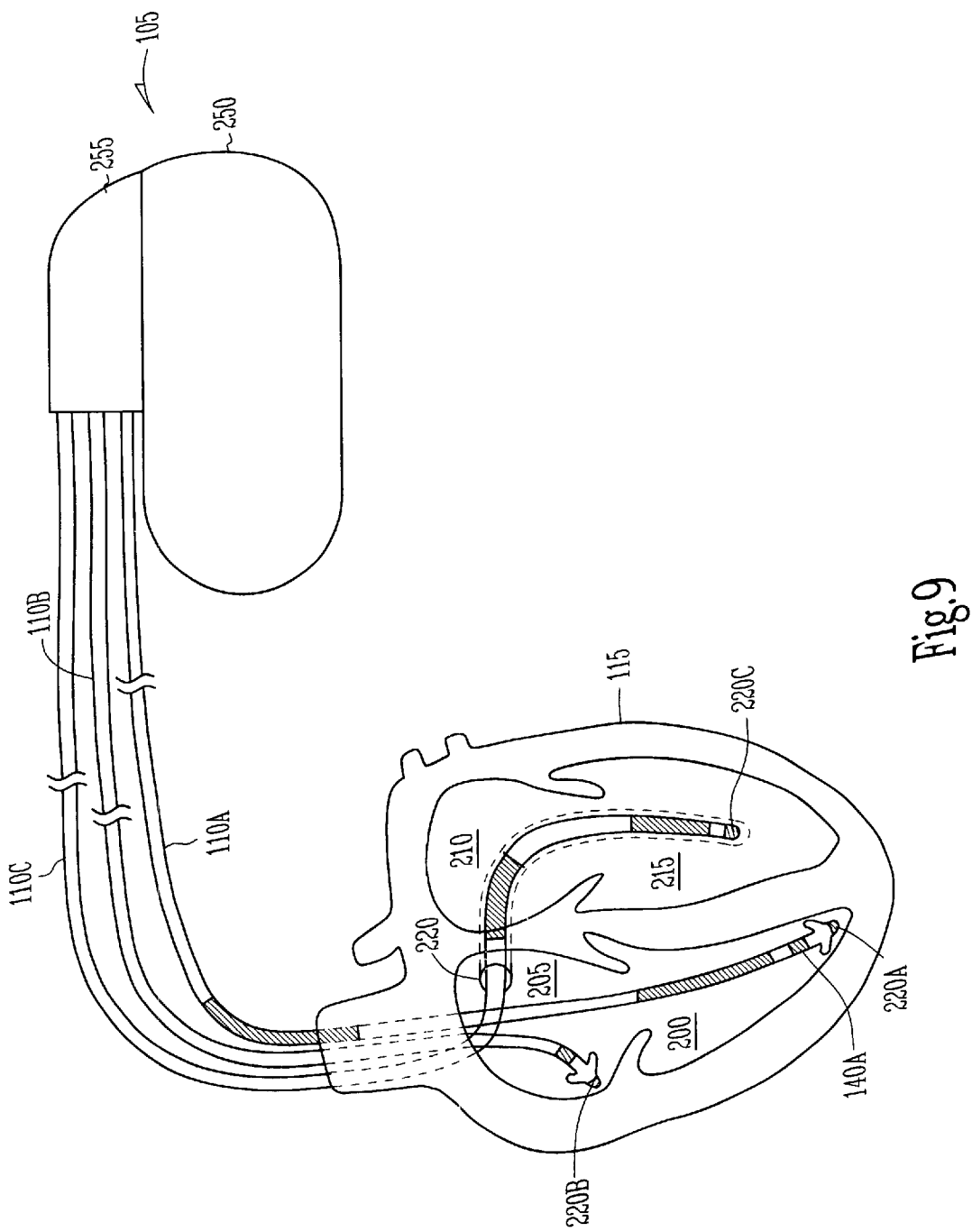
FIG. 9 is a schematic drawing illustrating generally, by way of example, an embodiment of using a cardiac rhythm management system coupled to a heart by right atrial, right ventricular, and left ventricular electrodes for pacing these chambers of the heart.

FIG. 9 is a schematic drawing, similar to FIG. 2, illustrating generally, by way of example, but not by way of limitation, another embodiment of device 105 coupled by a right atrial lead 110B to a heart 115, in addition to the ventricular leads 110A and 110C shown in FIG. 2, which includes a right atrium 205. In this embodiment, right atrial lead 110B includes electrodes (electrical contacts) disposed in, around, or near right atrium 205 of the heart 115, such as tip electrode 220B for delivering pacing therapy to the right atrium 205. The present method and apparatus will work in a variety of other configurations and with a variety of other electrical contacts or "electrodes."

Figure 10:
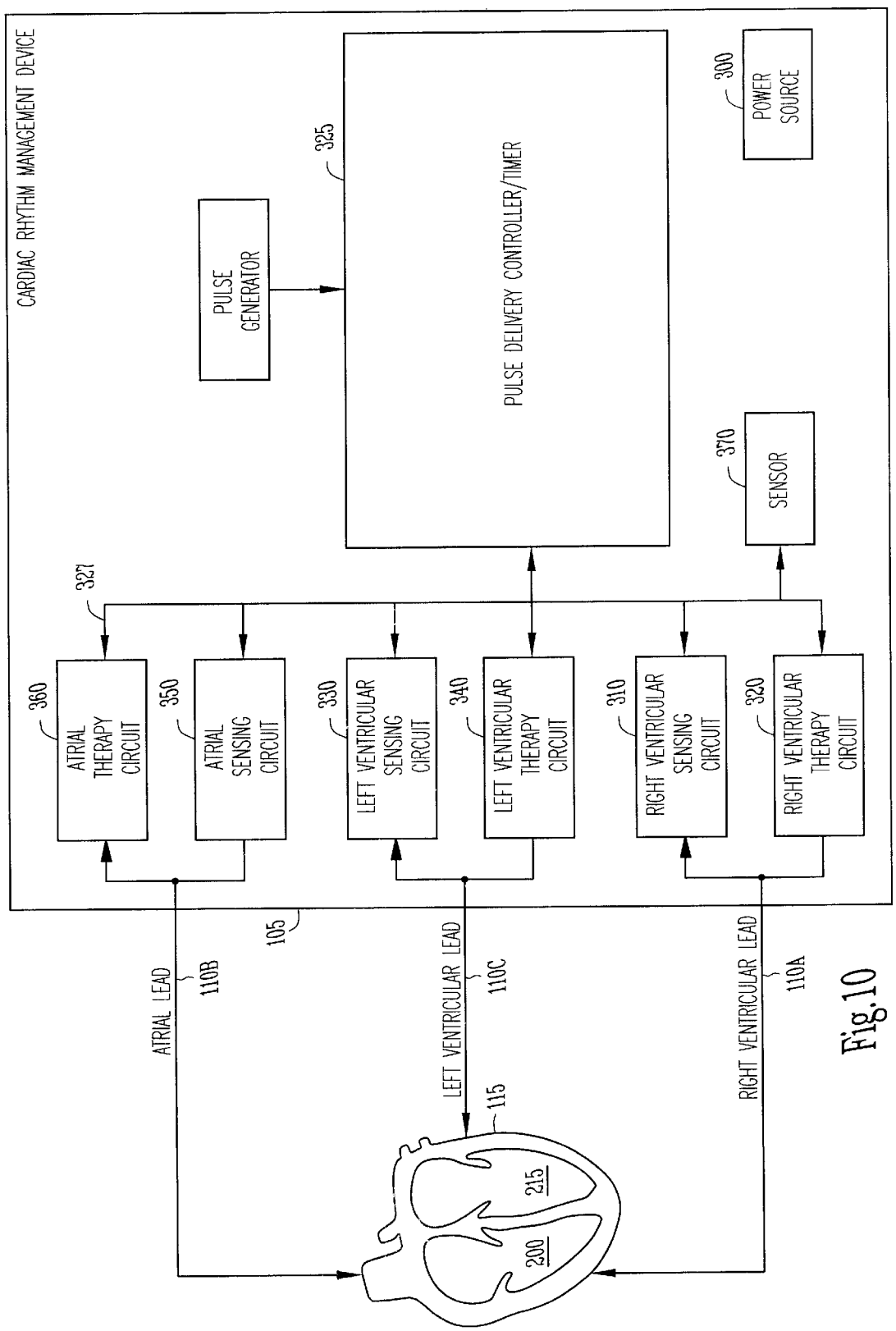
FIG. 10 is a schematic/block diagram illustrating generally another embodiment of portions of a cardiac rhythm management system showing interconnections between major functional components of the device when using right atrial, right ventricular and left ventricular electrodes coupled to a heart.

FIG. 10 is a schematic/block diagram, similar to FIG. 3, illustrating generally, by way of example, but not by way of limitation, another embodiment of portions of device 105, showing an atrial lead 110B coupled to a heart 115, in addition to the ventricular leads 110A and 110C shown in FIG. 3. Also shown is a atrial therapy circuit 360 and atrial a sensing circuit 350 connected via bus 327 to a programmable controller 325 for providing the coordination therapy to the heart. The programmable controller 325 provides staggered, nearly close, and non-overlapping pacing and recharge pulses to all three electrodes 110A–C.

Figure 11:
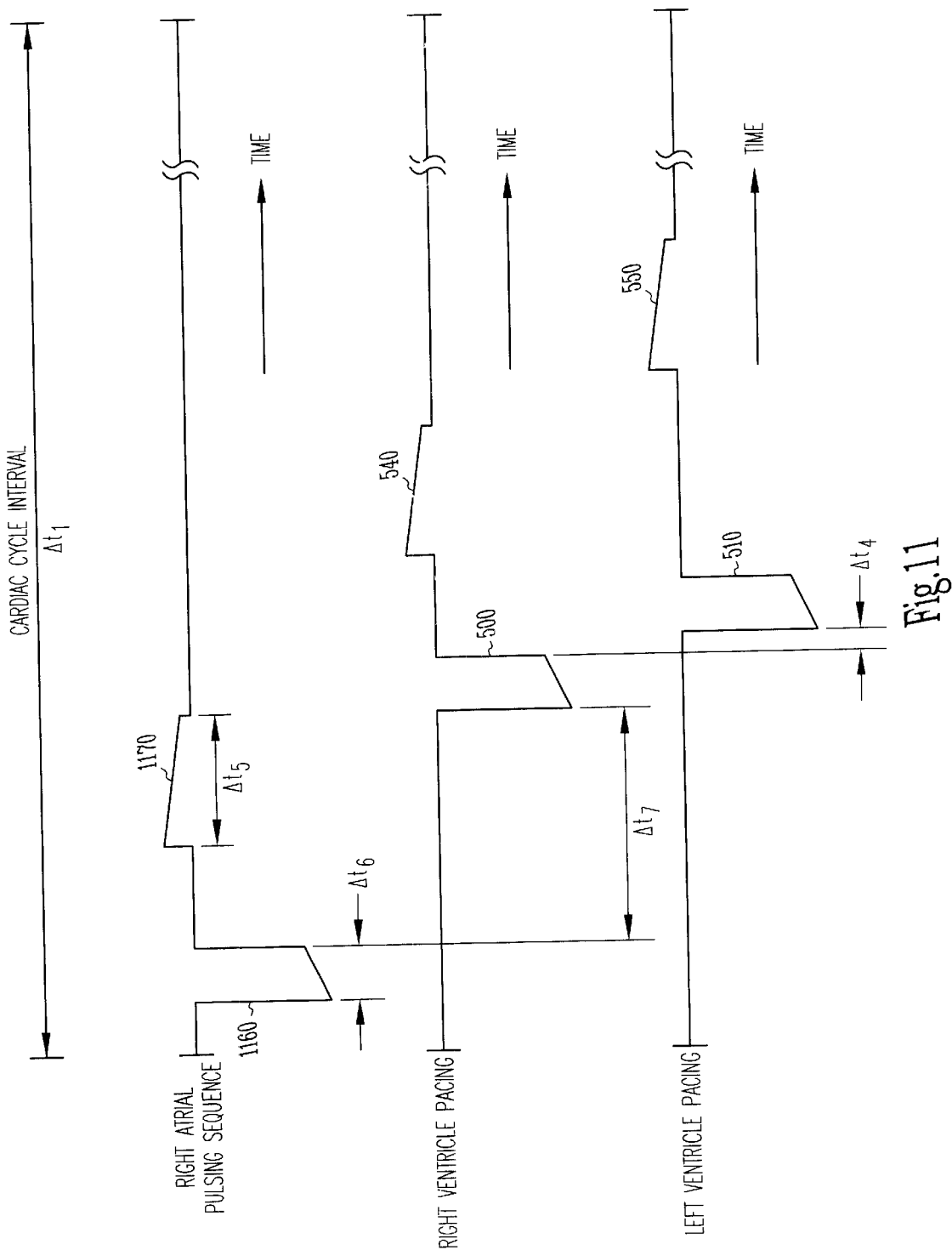
FIG. 11 is a schematic illustrating generally, by way of example, the ranges of time offsets and pulse durations issued between pulses (pace and/or recharge) associated with the right atrial, and right ventricular leads, and between pulses associated with right and left ventricular pulses to avoid any interactions between the leads.

FIG. 11 is a schematic, similar to FIG. 5, illustrating generally, by way of example, but not by way of limitation, another embodiment of the ranges of offsets and pulse durations used in providing an offset between the delivery of right atrial, left ventricle, and right ventricle pacing and discharging of associated recharge pulses to avoid any interaction between the electric fields surrounding the electrodes during pacing and discharging of the recharge pulses. FIG. 11, in addition to what is shown in FIG. 5, generally shows, by way of example, one embodiment of the offset $\Delta_{t7}$ between 10 to 400 milliseconds used between right atrial pacing pulse and the right ventricle pacing pulse to provide coordination therapy. Also shown in this embodiment, by way of example, are the right atrial pacing pulse 1160 duration 66 $t_6$, the recharge pulse 1170 duration $\Delta t_5$, and the offset $\Delta t_4$ introduced between the left and right ventricular pacing pulses 500 and 510.

Figure 12:
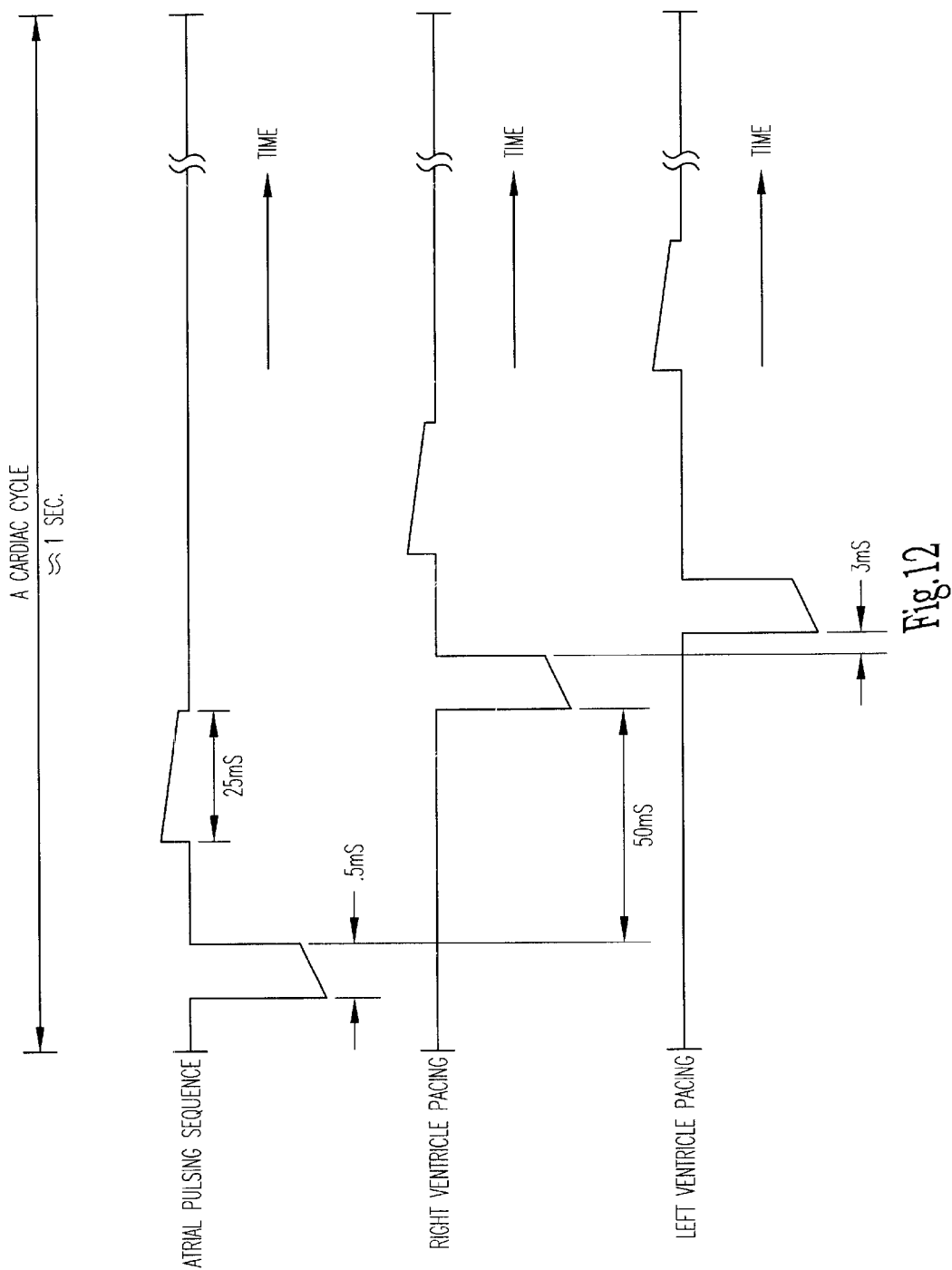
FIG. 12 is a schematic illustrating generally, by way of example, one embodiment of time offsets issued between a right atrial and right ventricular, and right and left ventricular pacing, and discharging of a recharge pulses associated with the pacing pulses to avoid any interactions between the leads and to provide a coordinated therapy to a heart.

FIG. 12 is a schematic, similar to FIG. 6, illustrating generally, by way of example, but not by way of limitation, one embodiment of issuing an offset of three milliseconds between right and left ventricular pacing pulses, and a 50 millisecond offset issued between the right atrial and right ventricular pacing pulses to generate contractions of three heart chambers, and to avoid any unwanted interactions between electric fields surrounding the electrodes at the three heart chambers during a coordination therapy. Also shown are one embodiment of atrial pacing pulse duration of 0.5 milliseconds and the atrial recharge pulse duration of 25 milliseconds.

Figure 13:
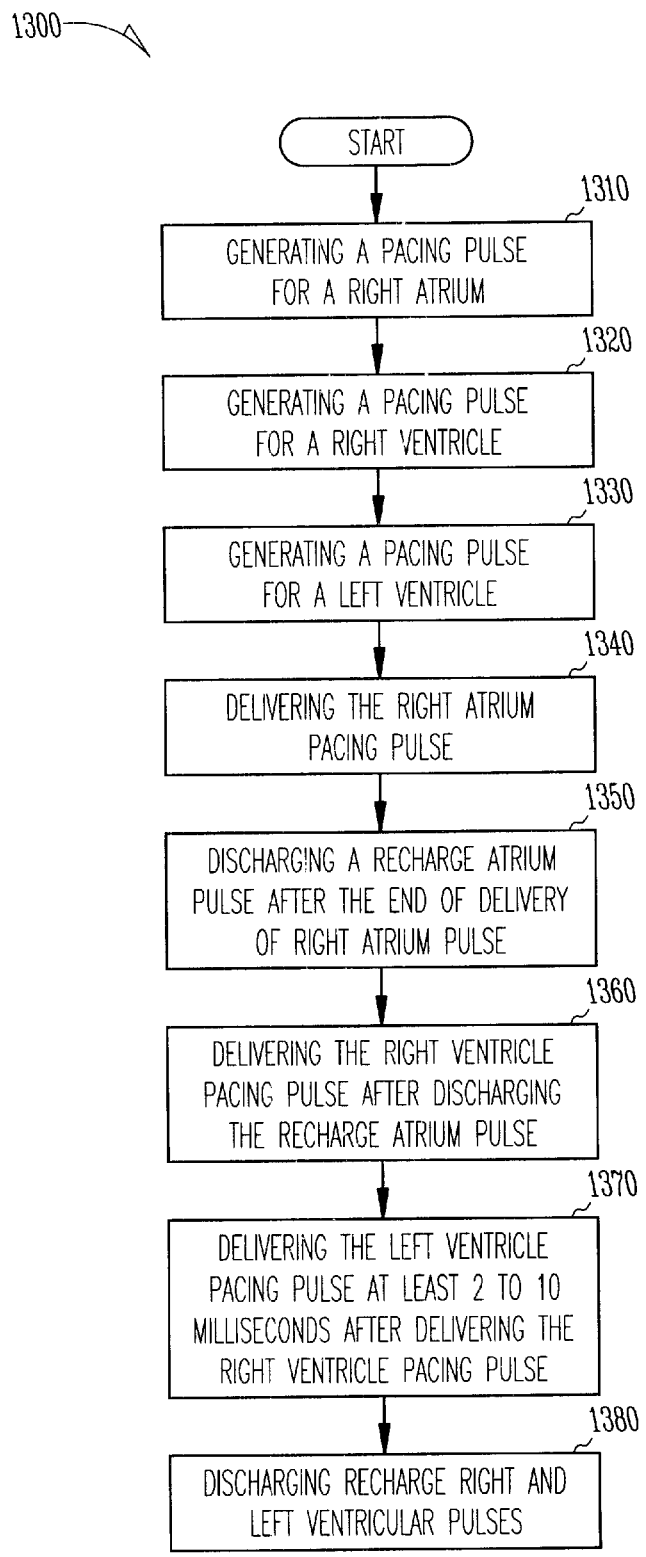
FIG. 13 is a flow chart illustrating generally, way of example, another embodiment of providing a coordinated therapy to a heart.

FIG. 13 is a flow chart, similar to FIG. 8, illustrating generally, by way of example but not by way of limitation, another embodiment of the various steps included in providing a coordinated therapy to a heart. The first step in the process of providing the coordinated therapy to the heart includes generating a right atrium, right ventricle and left ventricle pacing pulses 1310, 1320, and 1330. After generating the pacing pulses, a pulse delivery controller delivers the right atrium pacing pulse to a right atrium chamber of a heart 1340. Then the pulse delivery controller discharges a recharge atrium pulse after completing the delivery of the right atrium pulse such that the recharge and the pacing pulses are non-overlapping to avoid any interactions between electric fields surrounding the electrodes during pacing and discharging 1350. After discharging the recharge atrium pulse, the pulse delivery controller delivers the right ventricle pacing pulse to the right ventricular chamber of the heart 1360. Then the pulse delivery controller deliver the left ventricle pacing pulse to the left ventricular chamber of the heart at least 2 to 10 milliseconds after delivering the right ventricle pacing pulse such that the right and left ventricle pulses are substantially simultaneous and non-overlapping to avoid any interactions between electric fields surrounding the electrodes during pacing 1370. Then the pulse delivery controller discharges recharge right and left ventricular pulses from the right and left ventricular chambers of the heart such that they are non-overlapping to avoid any interactions between electric fields surrounding the electrodes during pacing and discharging 1380.

FIG. 13 is a flow chart, similar to FIG. 7, illustrating generally, by way of example but not by way of limitation, another embodiment of the steps of providing a coordinated therapy to a heart. In addition to what is shown in FIG. 7, FIG. 13 includes the steps of delivering and discharging right atrium pacing and recharge pulses.

Figure 14:
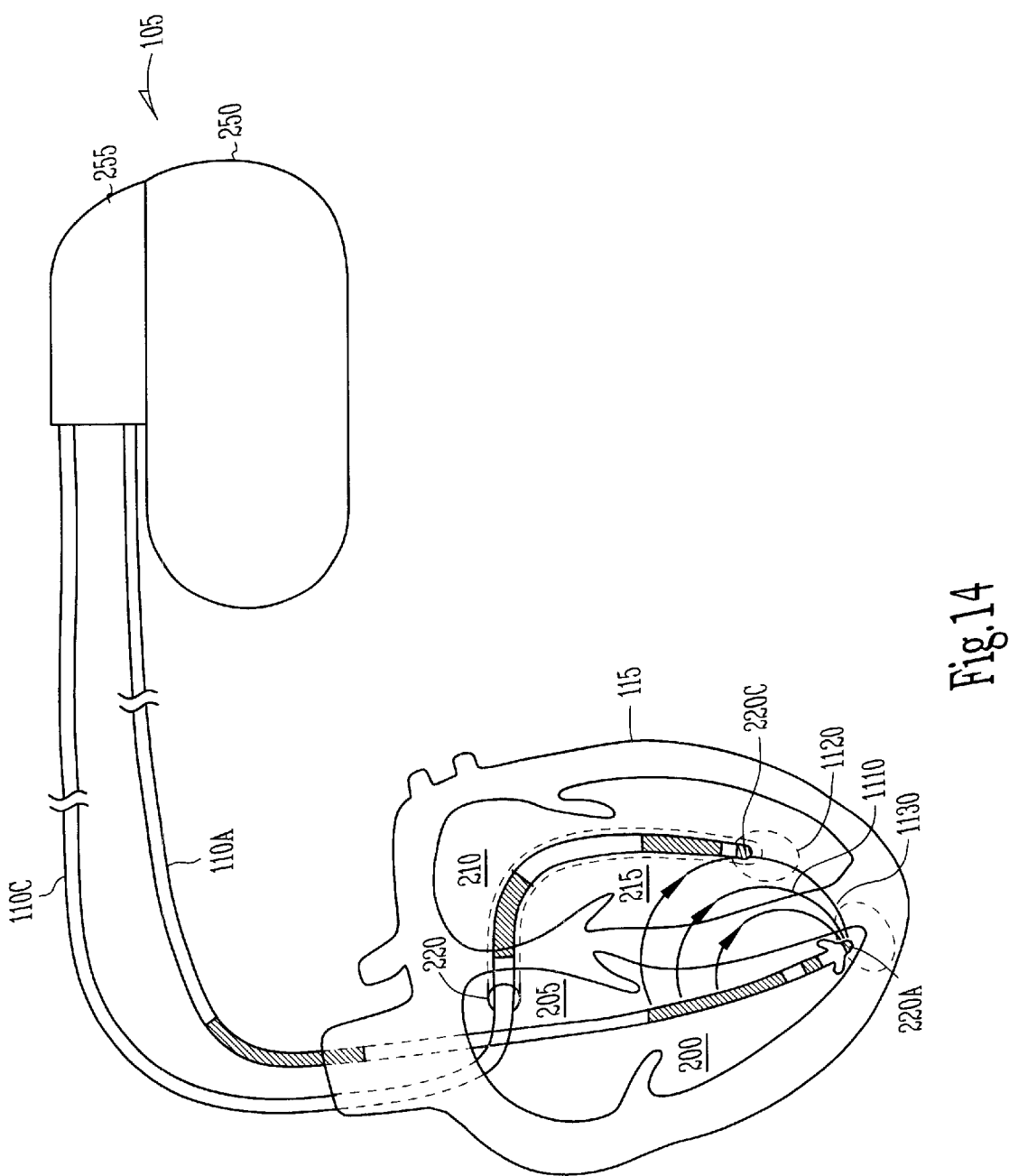
FIG. 14 is a schematic drawing illustrating generally one example of interactions taking place between electric fields at two pacing sites.

FIG. 14 is a schematic drawing showing generally one embodiment of an unwanted interactions 1130 taking place between the electric fields 1110 and 1120 surrounding the right ventricular lead 220A and left ventricular lead 220C, during simultaneous pacing of both the ventricles.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

CONCLUSION

The above-described system provides, among other things, an offset between pacing and recharge pulses using a pulse delivery controller during a coordination therapy. The pulse delivery controller, by issuing pulses and discharging recharge pulses in a desired sequence eliminates any interactions resulting between electric fields surrounding electrodes at different pacing sites of a heart. This issuing of pulses in a desired sequence ensures providing a required/programmed level of energy to the electrodes during a coordination therapy.

What is claimed is:

1. A cardiac rhythm management system, comprising:
   a pulse generator, for generating pulses;
   a first cardiac chamber electrode, coupled to the pulse generator, for delivering a first pulse, wherein the first pulse has a beginning and an end;
   a second cardiac chamber electrode, coupled to the pulse generator, for delivering a second pulse, wherein the second pulse has a beginning and an end; and
   a pulse delivery controller, coupled to the pulse generator, wherein the pulse delivery controller generates an offset between the end of delivery of the first pulse and the beginning of delivery of the second pulse such that the first and second pulses are substantially simultaneous and non-overlapping.

2. The system of claim 1, wherein the pulse generator generates pacing pulses.

3. The system of claim 1, wherein the pulse generator generates discharging recharge pulses.

4. The system of claim 1, wherein the first cardiac chamber is associated with right atrial and right ventricular chambers of a heart.

5. The system of claim 1, wherein the second cardiac chamber is associated with left atrial and left ventricular chambers of a heart.

6. The system of claim 1, wherein the offset is approximately in the range of 2 milliseconds to 10 milliseconds.

7. The system of claim 1, wherein the first cardiac chamber is associated with right atrial and ventricular chambers of a heart, and wherein the left cardiac chamber is associated with left atrial, and left ventricular chambers of the heart.

8. The system of claim 7, wherein at least one of the right and left atrial electrodes is a bipolar electrode and the other of the first and second electrodes is a unipolar electrode.

9. The system of claim 7, where a configuration of electrodes is selected from the group consisting of: (1) a bipolar right ventricular electrode and a unipolar left ventricular electrode, (2) a bipolar left ventricular electrode and a unipolar right ventricular electrode, (3) a bipolar right ventricular electrode and a bipolar left ventricular electrode, and (4) a unipolar right ventricular electrode and a unipolar left ventricular electrode.

10. The system of claim 7, in which the offset between the end of delivery of the left ventricular pulse and the beginning of delivery of the right ventricular pulse is approximately in the range of about 2 milliseconds to 10 milliseconds.

11. The system of claim 7, in which the offset between the end of delivery of the left atrial pulse and the beginning of delivery of left ventricular pulse is approximately in the range of about 2 milliseconds to 10 milliseconds.

12. The system of claim 7, in which the offset between the end of delivery of the right atrial and the beginning of delivery of the right ventricular pulses is approximately in the range of about 10 milliseconds to 400 milliseconds, and the offset between the end of delivery of the right ventricular and the beginning of delivery of the left ventricular pulses is approximately in the range of about 2 milliseconds to 10 milliseconds.

13. The system of claim 1, wherein the pulse delivery controller comprises a timer, wherein the timer generates an offset between the delivery of a first pulse associated with the first electrode and the delivery of a second pulse associated with the second electrode such that the pulses are substantially close and non-overlapping.

14. A cardiac rhythm management system, comprising:
a pulse generator for generating pacing pulses, and discharging recharge pulses;
first, second, and third electrodes, coupled to the pulse generator, where the first electrode adapted for being associated with a right ventricle of a heart, second electrode adapted for being associated with a left ventricle of the heart, and the third electrode adapted for being associated with a right atrium of the heart; and
a timer, coupled to the pulse generator, where the timer times delivery of the pacing pulses such that the pacing pulses associated with the first electrode are offset but non-overlapping with the pacing pulses associated with the second electrode, and the pacing pulses associated with the third electrode is offset but non-overlapping with the first and second electrodes, and wherein the timer further times discharging of the recharge pacing pulses associated with the pacing pulses of the first, second and third electrodes such that the discharging of recharge pulses are offset but non-overlapping with the recharge and pacing pulses of the first, second and third electrodes.

15. A cardiac rhythm management system, comprising:
pulse generator means;
a first cardiac chamber electrode coupled to the pulse generator means for delivering a first pulse, wherein the first pulse has a beginning and an end;
a second cardiac chamber electrode coupled to the pulse generator means for delivering a second pulse, wherein the second pulse has a beginning and an end; and
means for generating an offset between the end of delivery of the first pulse and the beginning of delivery of the second pulse such that the first and second pulses are substantially simultaneous and non-overlapping.

16. A method, comprising:
generating a first pacing pulse for a first cardiac chamber of a heart, where the first pacing pulse includes a beginning and an end;
generating a second pacing pulse for a second cardiac chamber of the heart, where the second pacing pulse includes a beginning and an end; and
delivering the first and second pacing pulses to the first and second cardiac chambers of the heart respectively, wherein there is an offset between the end of delivery of the first pacing pulse and the beginning of delivery of the second pacing pulse, wherein the first and second pacing pulses are substantially simultaneous and non-overlapping.

17. The method of claim 16, wherein the first and second cardiac chambers are associated respectively with the right and left atrial chambers of the heart.

18. The method of claim 16, wherein the first and second cardiac chambers are associated respectively with the right and left ventricular chambers of the heart.

19. The method of claim 16, wherein the first and second pacing pulses are associated respectively with the right and left ventricular chambers of the heart, and further the first and second pacing pulses are associated with right and left atrial chambers of the heart.

20. The method of claim 16, wherein delivering the first and second pacing pulses includes an offset approximately in the range of 2 milliseconds to 10 milliseconds between the end of delivery of the first atrial pacing pulse and the beginning of delivery of the second atrial pacing pulse.

21. A method of delivering a coordinated pacing therapy to a heart, the method comprising:
generating a right ventricular pacing pulse having a pulse duration approximately in the range of 0.05 milliseconds to 2 milliseconds;
generating a left ventricular pacing pulse having a pulse duration of approximately in the range of 0.05 milliseconds to 2 milliseconds;
delivering the right ventricular pacing pulse to the right ventricular chamber of a heart;
delivering the left ventricular pacing pulse to the left ventricular chamber of the heart such that it is greater than or equal to 2 milliseconds and less than or equal to 10 milliseconds after delivering the right ventricular pacing pulse to the heart, wherein the right and left ventricular pacing pulses are substantially simultaneous and non-overlapping; and discharging right and left ventricular recharge pulses, wherein the discharging of the right and left ventricular recharge pulses are non overlapping, and wherein the discharging of the recharge pulses are further non overlapping with the right and left ventricular pulses.

22. A method of delivering a coordinated pacing therapy to a heart, the method comprising:

generating a right atrial pacing pulse for a right atrium having a pulse duration of approximately in the range of 0.05 milliseconds to 2 milliseconds;

generating a right ventricular pacing pulse for a right ventricle having the pulse duration of approximately in the range of 0.05 milliseconds to 2 milliseconds;

generating a left ventricular pacing pulse for a left ventricle having the pulse duration of approximately in the range of 0.05 milliseconds to 2 milliseconds;

delivering the right atrial pacing pulse;

discharging a right atrial recharge pulse after completing the delivery of the right atrial pacing pulse such that it is non-overlapping with the right atrial pacing pulse;

delivering the right ventricular pacing pulse such that it is approximately in the range of 2 milliseconds to 10 milliseconds after delivering the right atrial pacing pulse, and after completing the discharge of the right atrial recharge pulse;

delivery the left ventricular pulse such that it is approximately in the range of 2 milliseconds to 10 after delivering the right ventricular pacing pulse, and such that the right and left ventricular pacing pulses are substantially simultaneous and non-overlapping; and discharging right atrial, right ventricular and left ventricular recharge pulses such that they are non over lapping, and further the discharging of the right atrial, right ventricular, and left ventricular recharge pulses are non overlapping with the right atrial, right ventricular, and right ventricular pacing pulses.

* * * * *

UNITED STATES PATENT AND TRADEMARK OFFICE
CERTIFICATE OF CORRECTION

PATENT NO.    : 6,363,278 B1
DATED         : March 26, 2002
INVENTOR(S)   : Jeffrey E. Stahmann, Andrew P. Kramer and Julio C. Spinelli It is certified that error appears in the above-identified patent and that said Letters Patent is hereby corrected as shown below:

<u>Column 14,</u>
Line 9, delete "delivery" and insert -- delivering --, therefor.
Line 10, insert -- milliseconds -- between "10" and "after", therefor.
Line 15, delete "non over lapping" and insert -- non-overlapping --, therefor.
Lines 16-17, delete "non overlapping" and insert -- non-overlapping --, therefor.

Signed and Sealed this

Eighth Day of October, 2002

*Attest:*

*Attesting Officer*

JAMES E. ROGAN
*Director of the United States Patent and Trademark Office*